United States Patent
Muntermann (10) Patent No.: US 10,376,709 B2
(45) Date of Patent: Aug. 13, 2019

(54) APPARATUS FOR NUCLEAR MAGNETIC RESONANCE THERAPY

(71) Applicant: Axel Muntermann, Wetzlar (DE)

(72) Inventor: Axel Muntermann, Wetzlar (DE)

( * ) Notice: Subject to any disclaimer, the term of this patent is extended or adjusted under 35 U.S.C. 154(b) by 0 days.

(21) Appl. No.: 16/300,287

(22) PCT Filed: May 9, 2017

(86) PCT No.: PCT/EP2017/061037
§ 371 (c)(1),
(2) Date: Nov. 9, 2018

(87) PCT Pub. No.: WO2017/194530
PCT Pub. Date: Nov. 16, 2017

(65) Prior Publication Data
US 2019/0134418 A1 May 9, 2019

(30) Foreign Application Priority Data
May 10, 2016 (DE) .......... 10 2016 108 601

(51) Int. Cl.
*A61N 2/02* (2006.01)
*A61N 2/00* (2006.01)
*G01R 33/34* (2006.01)
*G01R 33/381* (2006.01)

(52) U.S. Cl.
CPC .......... *A61N 2/02* (2013.01); *A61N 2/004* (2013.01); *G01R 33/34007* (2013.01); *G01R 33/34061* (2013.01); *G01R 33/381* (2013.01)

(58) Field of Classification Search
CPC .......... A61N 2/02; A61N 2/06; A61B 5/055
See application file for complete search history.

(56) References Cited

U.S. PATENT DOCUMENTS

| | | | |
|---|---|---|---|
| 5,221,902 A | 6/1993 | Jones et al. | |
| 5,261,403 A | 11/1993 | Saito et al. | |
| 5,441,495 A * | 8/1995 | Liboff | A61N 2/02 600/13 |
| 6,558,311 B1 | 5/2003 | Muntermann | |
| 8,845,508 B2 * | 9/2014 | Schneider | A61B 5/04009 600/14 |
| 2011/0118535 A1 | 5/2011 | Muntermann | |
| 2012/0286784 A1 | 11/2012 | Driemel | |

FOREIGN PATENT DOCUMENTS

| | | |
|---|---|---|
| DE | 19827736 A1 | 12/1999 |
| DE | 102009060544 A1 | 6/2011 |
| DE | 102011075454 A1 | 11/2012 |
| DE | 102008029415 | 5/2014 |
| JP | H1043159 A | 2/1998 |
| WO | 2008104522 A3 | 10/2008 |

* cited by examiner

*Primary Examiner* — Christine H Matthews
(74) *Attorney, Agent, or Firm* — Smartpat PLC (57) ABSTRACT

An apparatus for nuclear magnetic resonance therapy comprises a bed, two opposing sweep coils, as well as an upper coil and a lower coil for generating an alternating magnetic field.

13 Claims, 13 Drawing Sheets

APPARATUS FOR NUCLEAR MAGNETIC RESONANCE THERAPY

TECHNICAL FIELD

The invention relates to an apparatus for nuclear magnetic resonance therapy, i.e. an apparatus by means of which nuclear magnetic resonances can be achieve for therapeutic purposes in a tissue to be treated.

BACKGROUND

Apparatus for nuclear magnetic resonance therapy are known. For example, German Patent DE 10 2009 060 544 B2 discloses an apparatus by means of which nuclear magnetic resonance can be achieved in a tissue to be treated for therapeutic purposes.

The apparatus disclosed in this patent has the advantage that it is open to the top and the user does not have to lie in a kind of tube that accommodates a toroidal coil.

Nuclear magnetic resonance therapy apparatus typically operate with low field strengths compared to NMR imaging devices. In the region of the tissue to be treated, a field as homogeneous as possible is produced, with a field strength in the mT range. This field is composed of a base amount and an additional field that is swept by a certain amount, for example in a sawtooth-like manner. This field defines the static field in the sense of theory of nuclear magnetic resonances. Perpendicularly thereto, an alternating magnetic field is irradiated, at least during the falling flanks of the swept field, and the frequency of the alternating magnetic field is tuned to the field strength of the swept field in such a way that during sweeping each time the swept field drops, the spins in the tissue to be treated will flip over.

It has been proven scientifically that such a treatment allows to achieve regeneration of tissue damage, in particular of cartilage and bone damage. In the cosmetic field for the treatment of cellulite, this form of therapy can be applied as well.

Particularly great successes were achieved in the field of arthritis treatment. It has been shown that cartilage tissue is able to regenerate due to the treatment so that cartilage damage can be regenerated.

Especially in the treatment of arthritis it is desirable to provide the largest possible treatment volume, since cartilage damage often extends over many regions of the body, especially in elderly patients.

Documents U.S. Pat. Nos. 5,261,403 A and 5,221,902 A disclose NMR imaging devices comprising components overlapping the patient.

SUMMARY

Given this background, an object of the invention is to provide an apparatus for nuclear magnetic resonance therapy which provides the largest possible treatment volume and which allows the user to enter in the most comfortable and convenient way possible.

The apparatus should be well suited especially for arthritis patients with movement restrictions.

The object is achieved by an apparatus for nuclear magnetic resonance therapy according to claim 1.

Preferred embodiments and further refinements of the invention are specified by the subject-matter of the dependent claims.

The invention relates to an apparatus for nuclear magnetic resonance therapy, i.e. an apparatus known from the basic principle and described in the introductory part, which can be used to achieve nuclear magnetic resonances in the tissue to be treated by sweeping a magnetic field which extends as homogeneously as possible through a treatment volume and at the same time irradiating an alternating magnetic field perpendicularly thereto, at least while the swept field drops.

The field strength of the swept field is in particular between 0.1 and 100 mT, preferably between 0.3 and 3 mT. This is accompanied by a frequency of the alternating field from 1 to 100 mT, preferably from 10 to 100 kHz.

Maximum field strength of the alternating field is preferably between 0.1 and 100 mT, more preferably between 0.1 and 3 mT.

For accommodating a patient, the apparatus for nuclear magnetic resonance therapy comprises a bed which is preferably arranged in a substantially horizontal orientation. However it is likewise conceivable to have a type of reclining chair, i.e. in particular a bed having an upper part that is inclined at a steeper angle than the lower part.

On either side of the bed, a respective coil is arranged laterally thereto, in particular a sweep coil, so that a treatment volume is defined by the space between the coils.

These coils are preferably arranged substantially in a Helmholtz configuration, thus generating a substantially homogeneous field that extends across the bed.

Preferably, copper coils having 10 to 300 turns are used as the sweep coils.

The sweep field consisting of a base amount and a modulated amount, as described above, is preferably generated solely by the sweep coils.

However, it is likewise conceivable that the base amount of the sweep field is entirely or partly generated by permanent magnets which are preferably also arranged in the side parts of the apparatus for nuclear magnetic resonance therapy.

In order to generate nuclear magnetic resonances within the treatment volume defined between the sweep coils, an alternating magnetic field is generated perpendicular to the sweep field.

For this purpose, the apparatus of the invention for nuclear magnetic resonance therapy comprises a first coil for generating a magnetic field, in particular an alternating field, which first coil is arranged below the bed.

A second coil for generating a magnetic field, in particular an alternating field, is arranged above the treatment volume.

Thus, this second coil is preferably located above or directly adjacent to the sweep coils.

The first and second further coils for generating an alternating magnetic field are preferably also arranged in Helmholtz configuration. During treatment, they are located above and below the patient. As a result, an alternating magnetic field is generated in the treatment volume, which has a higher field strength within the entire treatment volume compared to a single coil for generating an alternating magnetic field over the entire treatment volume.

The invention thus relates to an apparatus for treatment using magnetic fields, by means of which nuclear magnetic resonances can be generated in the tissue to be treated, wherein a substantially static field is generated preferably by coils that are arranged laterally, and an alternating field is generated perpendicularly thereto using two coils, one of which is arranged below and one above the user.

However, a reversed arrangement in which the coils for generating the alternating field are located laterally and the coils for generating the substantially static field are located above and below the user is conceivable as well within the sense of the invention.

The coils for generating the alternating magnetic field have preferably substantially the same length as the sweep coils. More particularly, they have the same length as the sweep coils +/−20%.

In another embodiment of the invention, the second coil for generating the alternating magnetic field is configured to be pivoted upwards or to be raised.

In particular, the upper coil for generating an alternating magnetic field is hinged on the casing of a sweep coil and can be pivoted upwards about an angle of at least 30°, preferably at least 40°. Especially patients with restricted mobility can reach the bed more easily in this way.

In one embodiment of the invention, the upper or second coil for generating an alternating magnetic field is arranged in a ring-type casing that has an inner opening and preferably a substantially rectangular shape when seen in a plan view.

Thus, the casing forms kind of a frame which accommodates the upper coil for generating the alternating field.

This frame preferably has a diameter of less than 200 mm, more preferably less than 100 mm. Thus, there is a free area inside the frame, so that the apparatus for nuclear magnetic resonance therapy is largely open to the top despite of the upper coil. Patients lying in the apparatus of the invention will not feel so confined in this way.

An upper coil above the treatment volume preferably follows substantially the shape of the bed and in particular extends over a length of 70% of the bed surface.

The coils for generating the alternating magnetic field and/or for generating the sweep field may in particular be arranged in a casing that has mutually parallel sides in its main extension direction, in which the coils extend rectilinearly, while on the narrow sides the coils extend in arcuate manner, in particular in the form of a circular arc. The casing preferably has a central opening, at least partially.

In this manner, a large magnetic field adapted to the treatment volume located above a bed can be generated in a simple manner.

In a preferred embodiment of the invention, two coils, in particular a sweep coil and the second further coil which preferably serves to generate an alternating magnetic field, are mounted to an angular part that can be pivoted upwards.

So, according to this embodiment of the invention it is contemplated that two out of the total of four coils which serve to generate nuclear magnetic resonances in the treatment volume, are pivoted upwards together so that the user can easily enter the device which is preferably in form of a bed.

In particular it is contemplated that the angular part is coupled to the rest of the apparatus via a pivot joint.

In order to provide a large access area, the angular part is adapted for being pivoted upwards about an angle of at least 50°, preferably at least 70°, according to a preferred embodiment of the invention.

The angular part can be held in an upwardly pivoted position by means of springs, in particular by traction gas springs. Such springs are able to ensure easy pivoting up and down.

Preferably, the apparatus comprises at least two, more preferably four traction springs. This allows to ensure, for example for the event that one traction spring should fail, that the angular part with the two coils does not come down with its entire weight.

According to one refinement of the invention, the angular part comprises at least one operating unit, in particular a screen which may be provided in the form of a touch screen, for example.

The operating unit may in particular be arranged on an upper corner of the angular part, and according to a preferred embodiment it is inclined both with respect to the horizontal plane and with respect to the vertical plane, so that the operating unit is arranged obliquely so as to face the operator of the device.

More particularly, the surface of a screen may be inclined with respect to a vertical plane about an angle of 20° to 80°, preferably 30° to 70°.

The angular part may have further electronic control components arranged therein, in particular a control unit for controlling the coils. Heavy components of the control unit are preferably not arranged in the movable angular part, but rather below the bed surface of the apparatus.

In one refinement of the invention, at least one coil is embedded in a potting compound, in particular in a resin.

It is in particular contemplated that the coils are introduced in a casing preferably made of plastic material and potted using a potting compound.

The use of a potting compound prevents the coils from moving, in particular due to Lorentz forces. In particular annoying humming noises can be eliminated in this way.

Preferably a fiber-reinforced composite material, in particular GFRP or CFRP, is used as a plastic for the casing.

In a further embodiment of the invention, the apparatus comprises an exchangeable bed surface. The bed surface may thus be exchanged for another bed surface of a different shape or with other functional treatment components, such as straps for fixing a body part.

In a further embodiment of the invention, the apparatus comprises a lighting means of variable color, which is preferably provided in the form of an LED light strip.

It is particularly intended that the light color changes during operation of the apparatus, that is when nuclear magnetic resonances are generated.

Furthermore, the lighting means may be used to mark the treatment volume, for example by having two light strips arranged on the second further coil, which project lateral strips of light onto the bed surface.

In a further embodiment of the invention, the apparatus comprises a control unit which is used to measure the amperage of one of the coils and/or the frequency of an alternating field generated by at least one of the coils, at least upon start-up of the apparatus.

This embodiment of the invention makes use of the fact, with regard to the sweep field, that the field strength of the sweep field is a function of amperage.

Amperage measurement thus allows to check whether the field strength of the sweep field is within the target range.

If this is not the case, due to an error, achieving of a resonance condition in the treatment volume would not be guaranteed, and the apparatus will issue an error message and stop the treatment.

Preferably, the alternating magnetic field is also controlled in terms of its frequency.

According to a preferred embodiment of the invention, the frequency of the alternating field and/or the amperage is controlled during ongoing operation as well.

In a preferred embodiment of the invention, the checking of the amperage and/or the checking of the frequency of the alternating field is done individually for each coil. In the case of an error it is thus easily possible to localize the cause of error.

In a further embodiment of the invention, the apparatus comprises a sensor which is in particular configured as a switch and by means of which it is checked whether the apparatus is closed, i.e. in particular whether the angular part is in its pivoted-down position.

Thus, a treatment can be carried out only when the coils are in the correct position relative to each other and not when the apparatus is partially open.

In one embodiment of the invention, the control unit comprises a timer that stops the time when a treatment is interrupted and, when the apparatus is restarted, continues treatment until a total treatment duration is reached that has been entered or stored. This ensures that even in case of treatment interruptions the desired treatment duration is exactly achieved.

In one embodiment of the invention, the sweep coils are each arranged in a side part adjacent to the bed, and one of the side parts is configured for being lowered or pivoted upwards.

In a first embodiment of the invention, a side part which accommodates a sweep coil can be moved downwards, so that it preferably does not protrude substantially beyond the bed surface in the lowered state anymore. Once the side part has been lowered and the casing of the upper coil for generating the alternating field has optionally been pivoted upwards, the patient or user can easily get into the apparatus for nuclear magnetic resonance therapy.

Preferably, only one side part is configured for being lowered or pivoted upwards. Thus, the mechanism is only required in one side part, and the apparatus can be placed with the fixed side part against a wall, for example.

In one embodiment of the invention, a lower portion of the sweep coils has a rectilinear shape and an upper portion of the sweep coils has a curved shape. In particular, the sweep coils essentially have the shape of a segmental arc window. The contour of the sweep coils is thus composed of a rectangle and a circular arc or elliptic segment.

This shape approximates the anatomy of the user. In the rear and front areas, i.e. in those areas where the extremities are located during the treatment, a smaller treatment volume is needed than in a central area.

The segmental arc has in particular a radius between 1 and 2 m.

In one embodiment of the invention, the bed is part of a detachable module that can be turned around about 180° and which comprises at least the first coil for generating an alternating magnetic field. In particular, the module including the bed also includes the control unit for driving the coils, and an operating unit. The operating unit is preferably arranged on a front side or rear side.

The module comprising the bed and the control unit can be connected to the other coils, i.e. to the sweep coils and to the upper, second coil for generating an alternating magnetic field.

Depending on where the apparatus of the invention is placed, the module can be installed with the bed turned around about 180°, so that in particular the operating panel or a headrest of the bed will be arranged on the desired side.

In one embodiment of the invention, the side parts are configured in the form of a casing which accommodates a respective sweep coil. At least if a sweep coil on one side is configured for being lowered, a sweep coil casing is preferably arranged between two columns between which the sweep coil casing is lowered.

In a preferred embodiment of the invention, the treatment volume provided by the apparatus for nuclear magnetic resonance therapy is between 1.4 and 2.5 meters in length, between 0.4 and 1 m in width, and/or between 0.4 and 1 m in height.

BRIEF DESCRIPTION OF THE DRAWINGS

The subject-matter of the invention will now be explained in more detail with reference to the drawings of FIGS. 1 through 16.

FIGS. 1 through 7 shows a first embodiment of the invention, in which two coils are arranged in an angular part that can be pivoted upwards.

With reference to FIGS. 8 through 16, a further embodiment of the invention will be illustrated, in which one side part is configured for being lowered.

DETAILED DESCRIPTION

Figure 1:
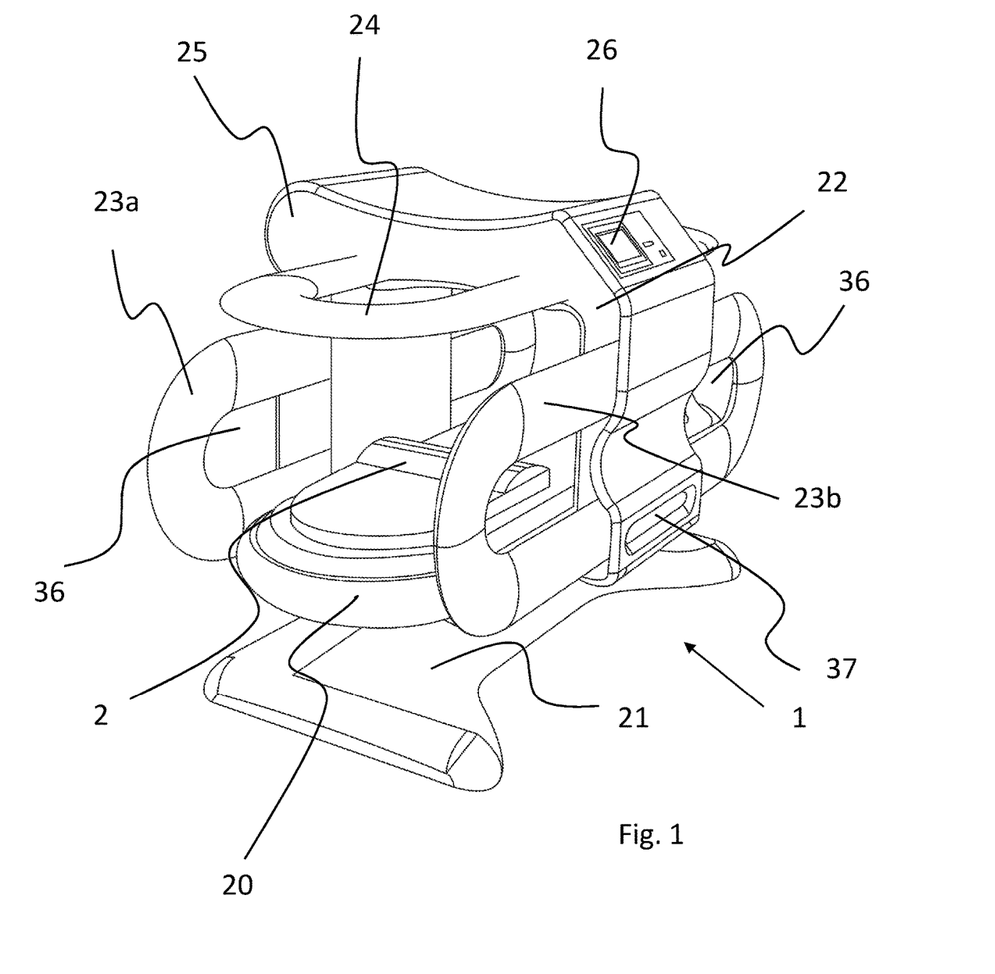
FIG. 1 and FIG. 2 are perspective views of an apparatus for nuclear magnetic resonance therapy.

FIG. 1 is a perspective view of a first embodiment of an apparatus 1 for nuclear magnetic resonance therapy.

The apparatus 1 for nuclear magnetic resonance therapy of this embodiment comprises a bed 20 with a bed surface 2, on which a user can lie down.

The bed 20 is disposed on a pedestal 21.

Adjacent to the bed 20, coil casings 23a, 23b are arranged, which in this exemplary embodiment comprise coils that are used to generate the sweep field.

Coil casings 23a, 23b have a substantially rectangular central portion with longitudinal edges of the casings 23b, 23b extending in parallel to one another. On the narrow sides, casing 23a, 23b have a curved design, in the present embodiment in the form of a circular arc.

In this manner it is possible to provide coil casings 23a and 23b which have substantially the same length as the bed surface 2 and which allow to provide a large treatment volume.

The treatment volume is defined by the volume between coil casings 23a and 23b and the area between bed surface 2 and coil casing 24.

The bed 20 accommodates a coil for generating an alternating magnetic field.

A further coil for generating an alternating magnetic field is located in coil casing 24, which is arranged above coil casings 23a and 23b.

Coil casing 24 also has an elongated shape with rounded narrow sides.

The bed 20 likewise has rounded narrow sides, and the bed accommodates a coil (not illustrated herein) with a shape that corresponds substantially to the coil in the coil casing.

The coil in coil casing 24 is also used to generate an alternating magnetic field.

The coil in bed 20 and the coil in coil casing 24 are arranged in a Helmholtz configuration, and an alternating magnetic field of homogeneous field strength is generated within the treatment volume.

In this way, whole-body treatment of a user is made possible in a simple manner.

All coil cases 23a, 23b, 24 have an opening 36 which in particular is intended to counteract claustrophobia of the user during the treatment.

In order to be able to get into the apparatus, the apparatus 1 of this exemplary embodiment comprises an angular part 22 which is arranged substantially centrally and which can be pivoted upwards about pivot joint 25 provided in the form of a hinge.

Mounted to the angular part 22 is the coil casing 24 of the upper coil above the treatment volume and the coil casing 23b of a sweep coil on the front side thereof.

When the angular part 22 is being pivoted upwards, both the coil casing 23b and the coil casing 24 will simultaneously be pivoted upwards and the user can easily reach the bed surface 2.

A handle 37 is provided in the lower portion of angular part 22 to allow to easily open and close the apparatus 1.

Angular part 22 extends only across a portion of the opening 36.

A screen 26 is located at an upper corner of the angular part 22 and is preferably designed as a touch screen. The control unit (not shown) may also be located in the angular part.

The screen or surface of the screen 26 is inclined relative to a vertical plane at an angle of 30° to 70° in order to enable to easily reach the screen, which is preferably provided in the form of a touch screen.

Other control components such as a card reader may also be arranged in this area.

The bed surface 2 may be removed and exchanged for another bed surface (not illustrated) which comprises further treatment components.

Figure 2:
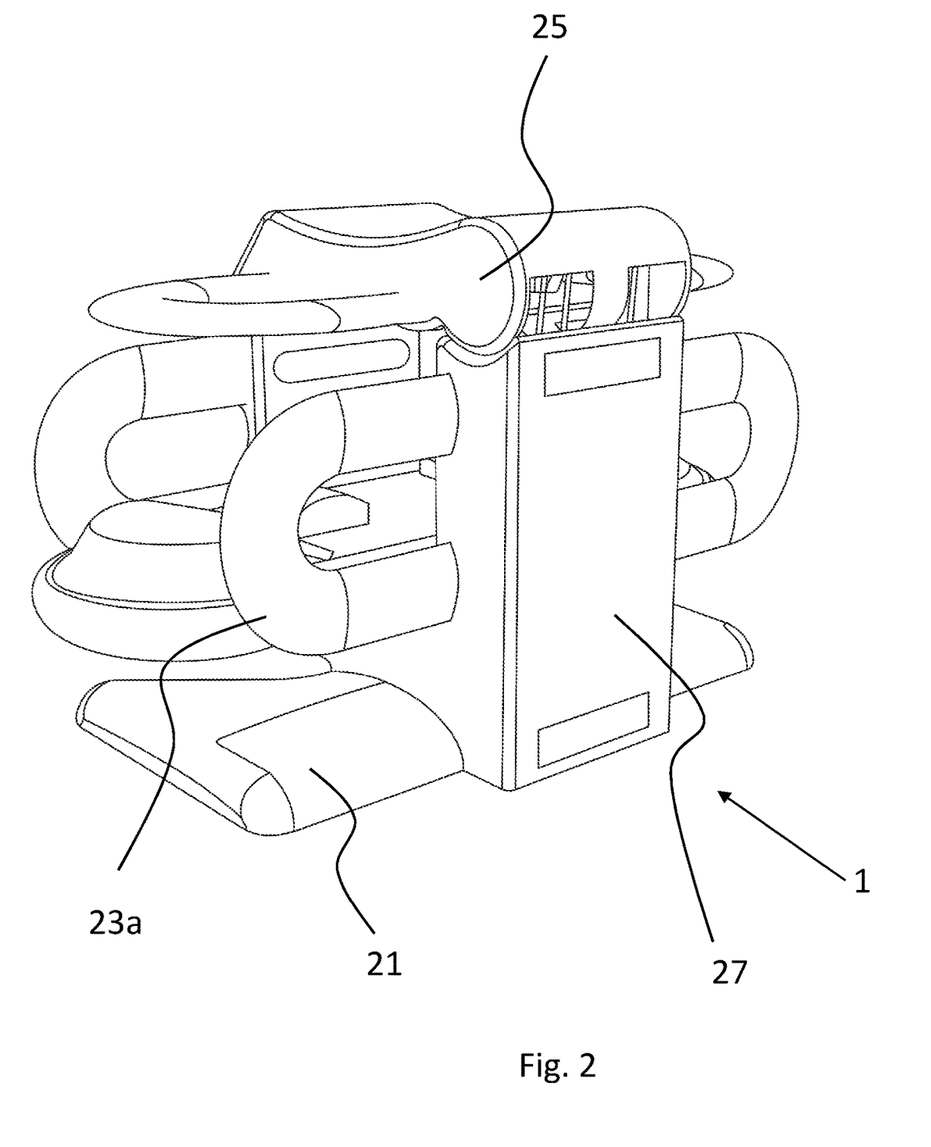

FIG. 2 is a perspective view of the rear side of the apparatus 1 illustrated in FIG. 1.

As can be seen in particular in this view, the apparatus 1 comprises a rear part 27 connected to the pedestal 21, and mounted to the rear part is coil casing 23a on the one hand, and pivot joint 25 on the other hand.

Rear part 27 extends centrally upwards in this embodiment, as a type of column.

It will be understood that control components of the apparatus 1 may be arranged in the rear part 27 as well.

Figure 3:
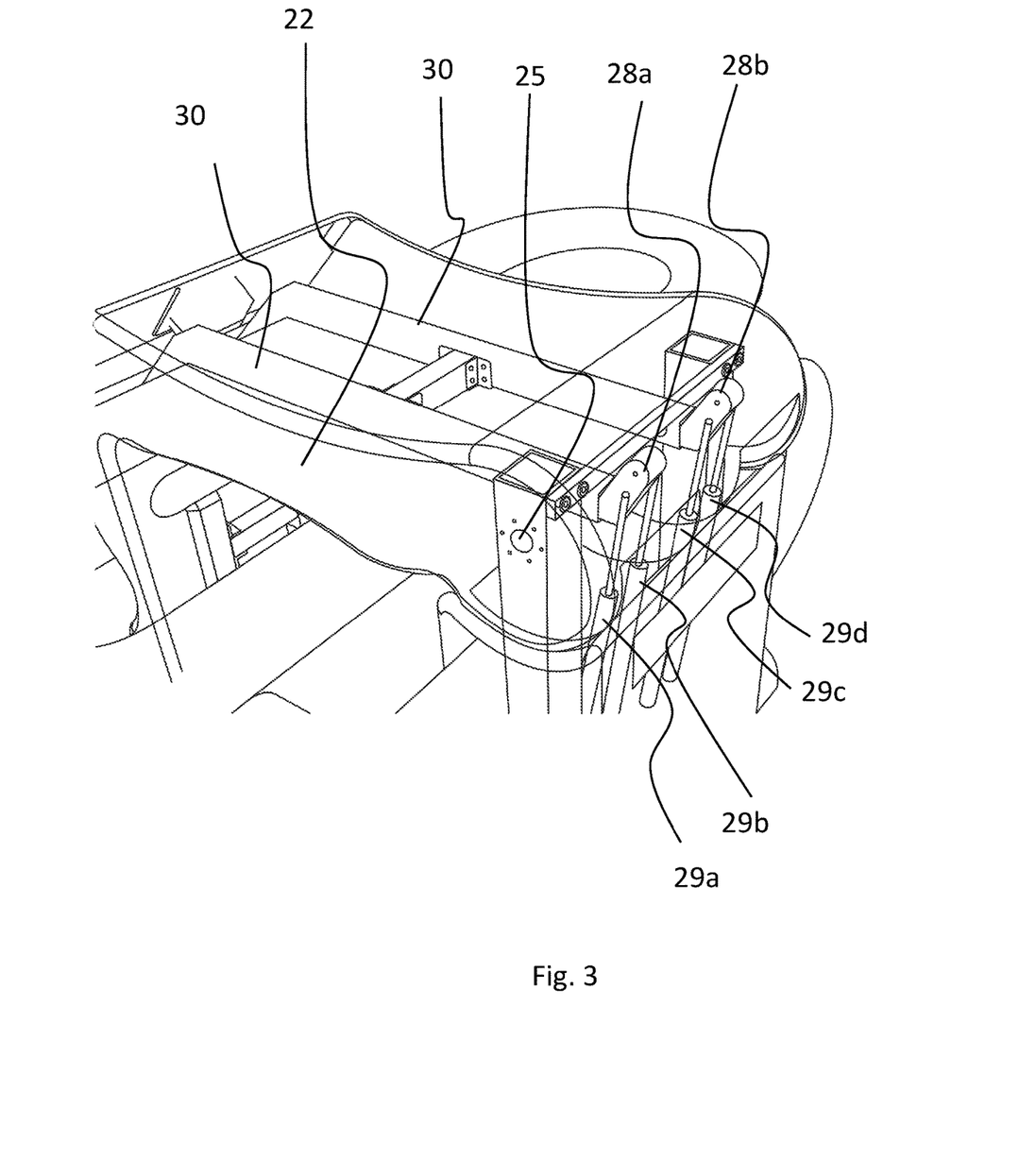
FIG. 3 is a wireframe view of a detail.

FIG. 3 is a perspective wireframe view which in particular illustrates the hinge 25.

Angular part 22 consists of a housing in which beams 30 are embedded, preferably metal beams 30.

These beams 30 are pivotally mounted to pivot joint 25.

On the side of the pivotal axis opposite to beam 30, a respective arm 28a, 28b is provided.

Each of arms 28a and 28b is connected to two traction gas springs 29a, 29b, and 29c, 29d, respectively.

Traction gas springs 29a-29d allow the angular part 22 to be easily pivoted upwards. Due to the pivoting downwards of the arms 28a and 28b associated therewith, the lever arm is extended so that in the fully opened state the traction gas springs 29a-29d exert a higher force than in the closed state of the apparatus and the apparatus will remain open automatically.

Figure 4:
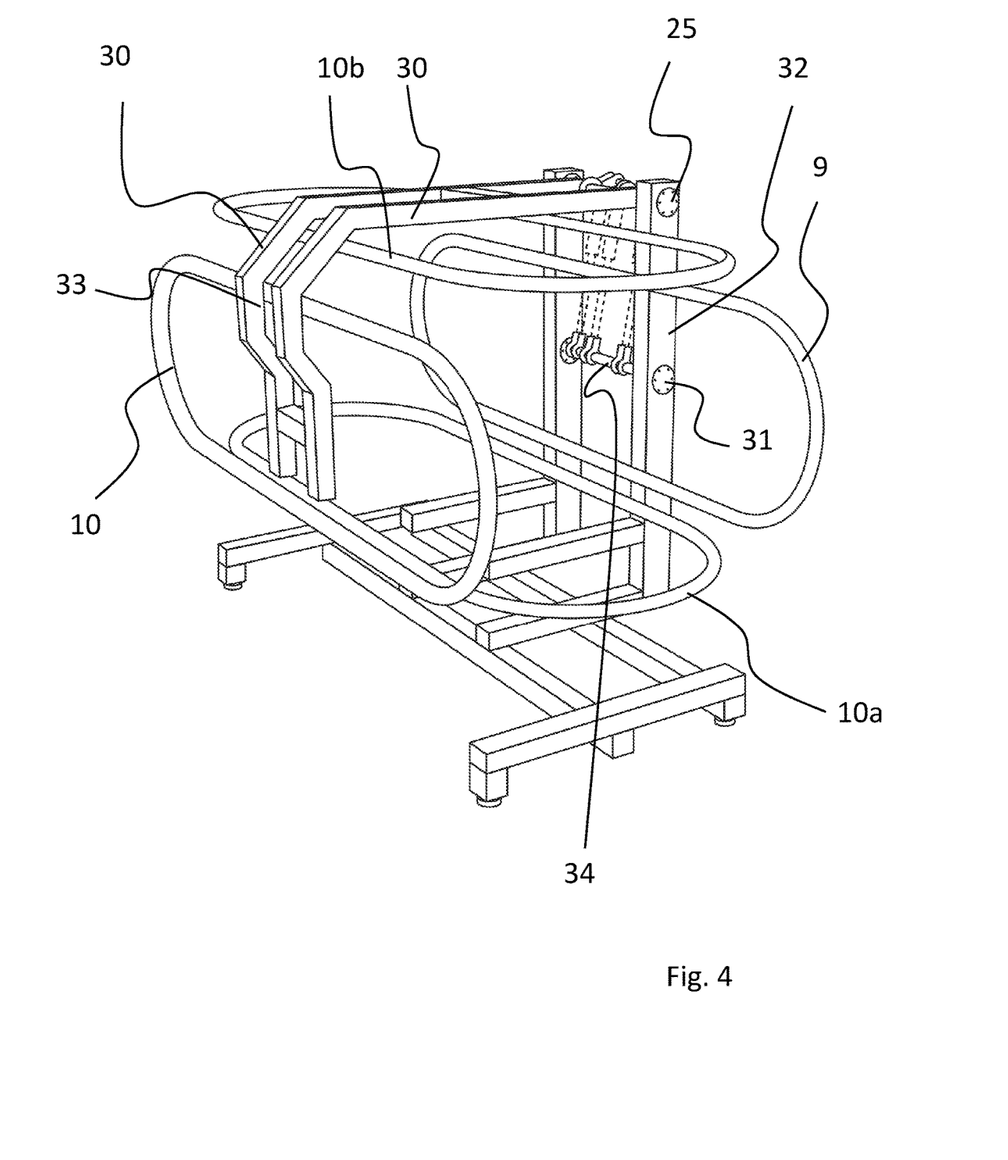
FIG. 4 shows the apparatus without housing.

FIG. 4 shows a perspective view in which all housing components and parts of the bed have been omitted.

Thus, coils 9 and 10 can be seen, which are arranged in a Helmholtz configuration and serve to generate the sweep field.

Coil 10a arranged below the bed and coil 10b arranged above the bed are used to irradiate an alternating field, that extends perpendicularly to the sweep field.

Beams 30 can be seen, which are of angular shape and are mounted to pivot joint 25.

Below pivot joint 25, a rod 34 is mounted, and the opposite ends of the traction gas springs are mounted to this rod thus defining a further pivot joint 31.

A frame 32 comprises support beams for both the rear part and the bed.

Beams 30 which are connected to one another and hinged to the frame 32 form a bulge 33 at the front side, behind of which an upper portion of the coil 10 extends.

The metal parts of the frame 32 and of the beams 30 may be electrically isolated from each other to minimize induction of currents, as is suggested according to one embodiment of the invention.

Figure 5:
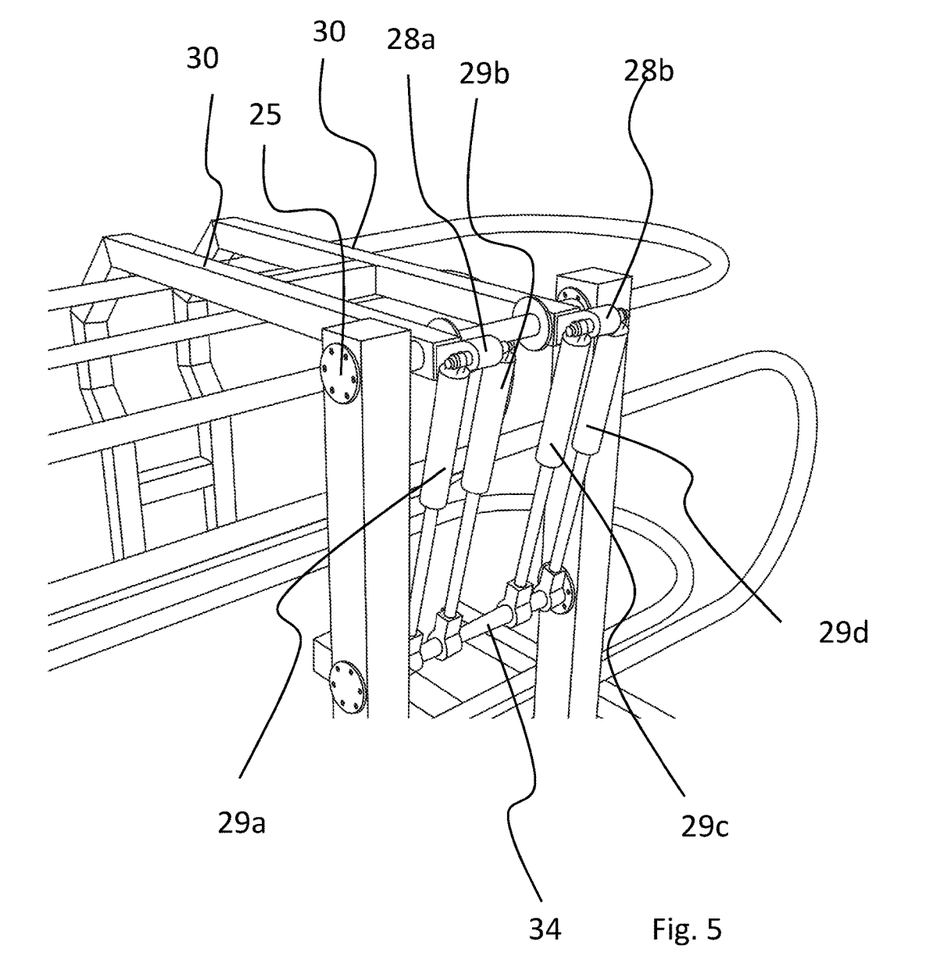
FIG. 5 is a view of a detail of FIG. 4.

FIG. 5 shows a detail of FIG. 4, in which the region of pivot joint 25 is clearly visible now, seen from the rear side.

In particular the rear arms 28a and 28b opposite beams 30 can be seen, to which the traction gas springs 29a-29d are mounted.

Furthermore, the rotatable rod 34 can be seen, which serves as a counter bearing for the lower ends of gas springs 29a-29d.

It will be understood that instead of a rotatable rod it is likewise possible, as an alternative, that each lower end of a traction gas spring 29a-29d is rotatably mounted on the rod.

Two traction gas springs are provided for each arm 28a, 28b. The use of a plurality of traction gas springs is particularly advantageous, since even in the case of failure of a traction gas spring, the angular part cannot come down with its entire weight, which could otherwise entail a risk of injury.

Figure 6:
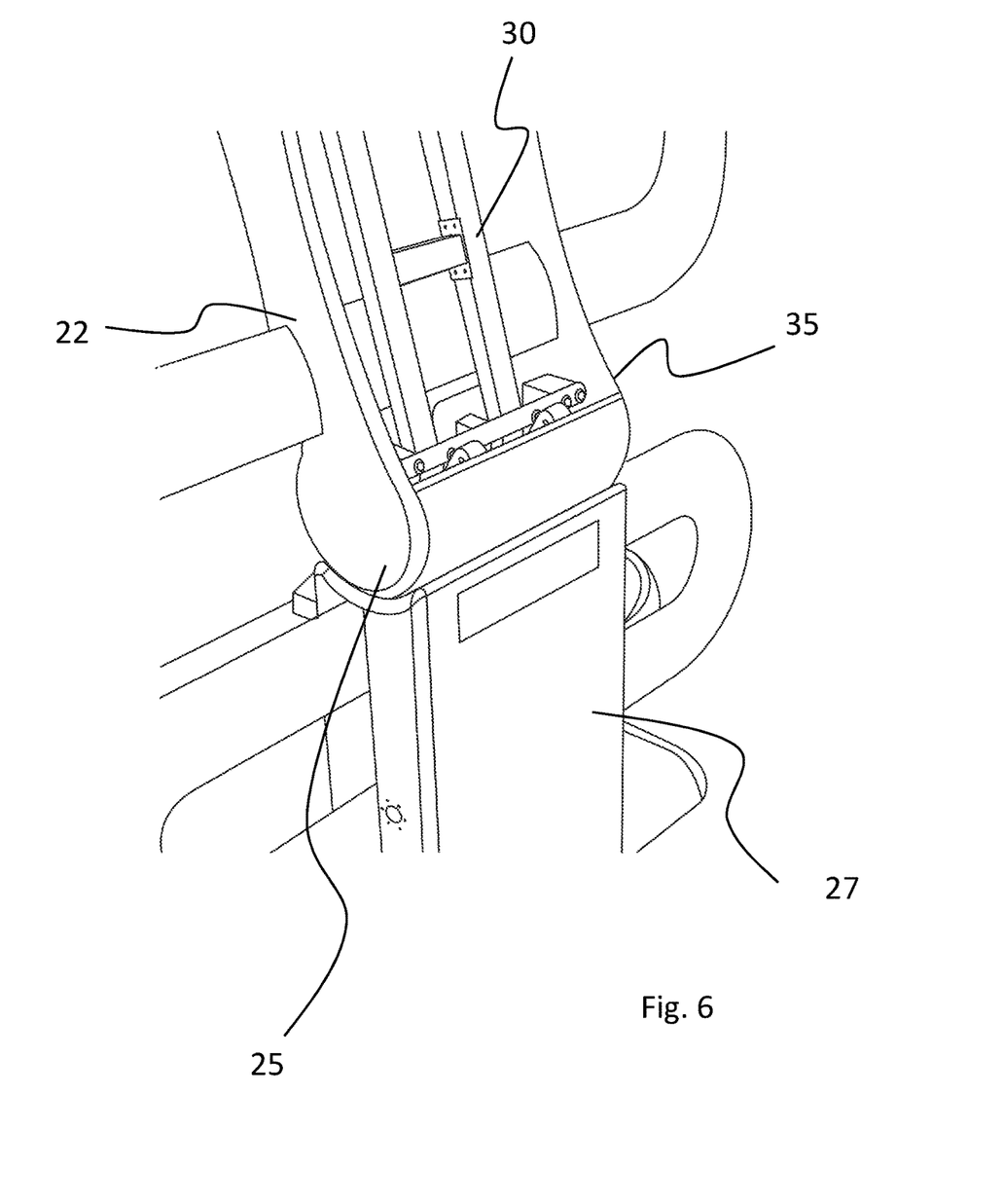
FIG. 6 is a detailed view of the pivot joint of the apparatus.

FIG. 6 is a wireframe view of the region of pivot joint 25.

The housing part 35 of angular part 22 can be seen extending around the beams 30. Pivot joint 25 is shown in the open state in this view.

Housing part 35 has a circular cylindrical shape in the region of pivot joint 25 and rotates in a corresponding recess of rear part 27.

Figure 7:
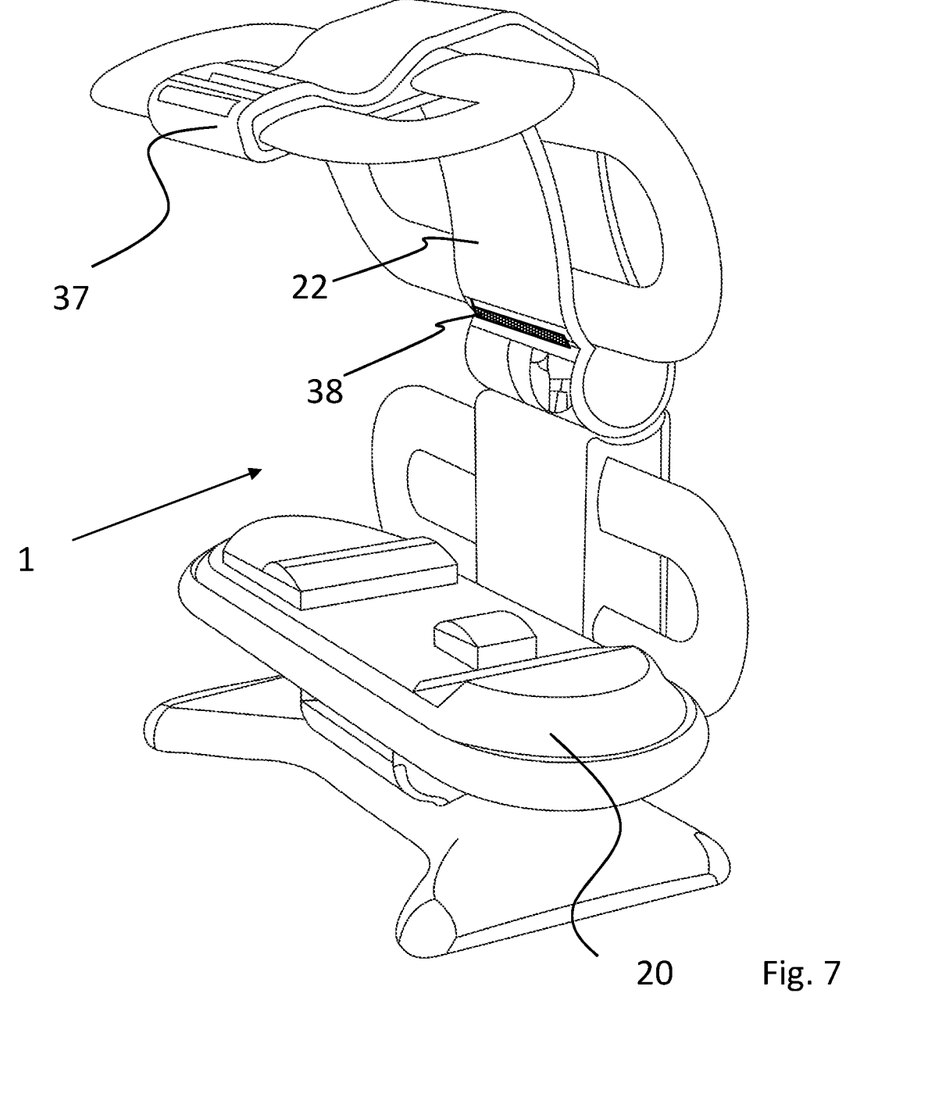
FIG. 7 is a perspective view in which the apparatus is illustrated in its open state.

FIG. 7 is a perspective view of the apparatus 1 for nuclear magnetic resonance therapy in its opened state.

As can be seen, the angular part 22 which carries two coils has been pivoted upwards about almost 90°. This ensures that the treatment volume is easily accessible.

According to one embodiment of the invention, provisions may be made for adjustment of the opening angle by the operator of the apparatus 1, for example to be able to adjust the maximum height of the handle 37 for different operators.

Furthermore, in this exemplary embodiment, the angular part 22 comprises opposing light strips 38. Only one light strip 38 can be seen in this view. An opposite light strip is disposed above the bed surface on the other side of the angular part 22. Light strips 38 are preferably designed as LED lighting of variable color.

Light strips 38 may serve to mark the treatment volume and may also indicate whether the apparatus 1 is in operation. For example, upon start-up of the apparatus 1 the light color may change.

Figure 8:
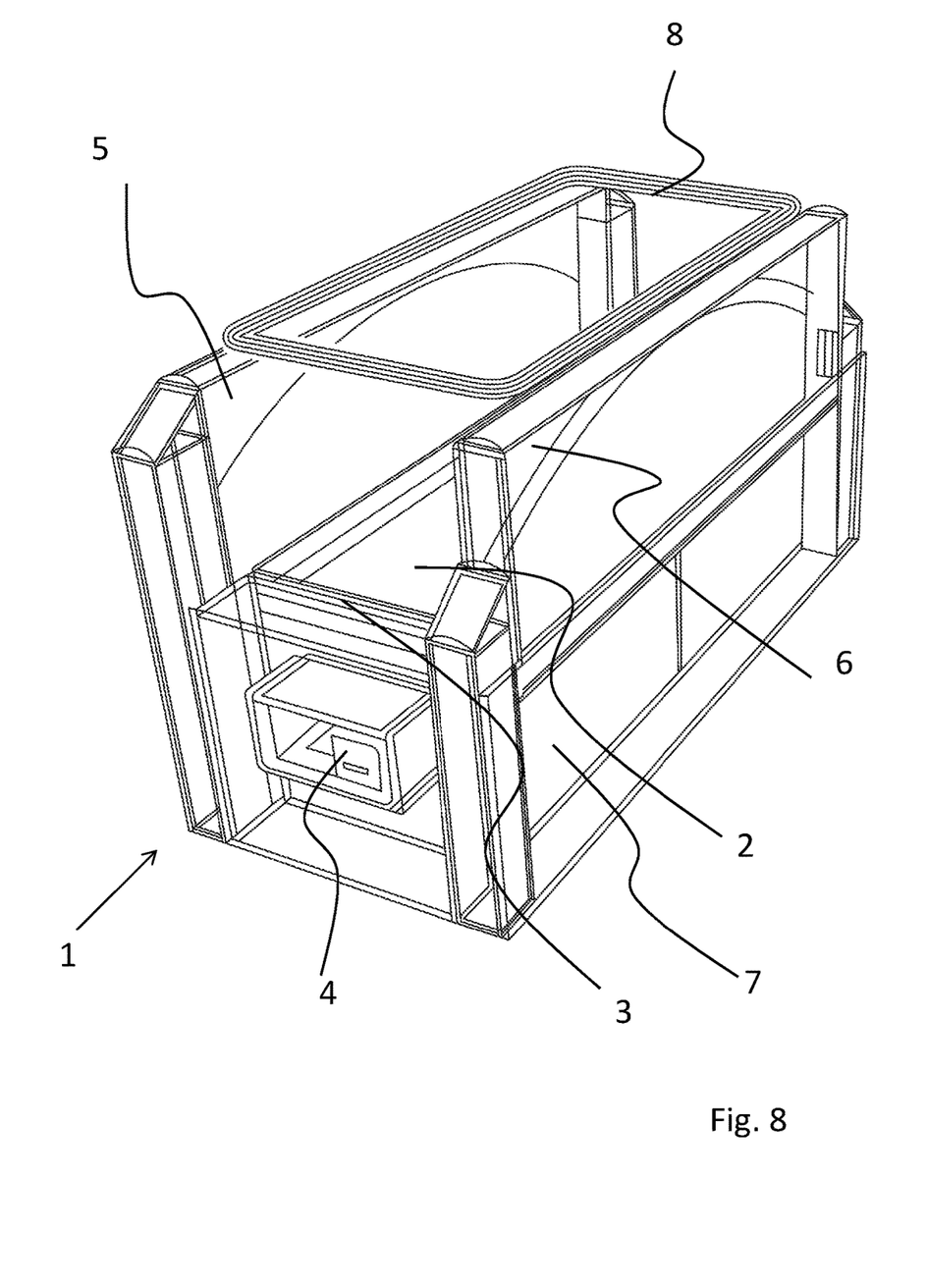
FIG. 8 shows a perspective view of an apparatus for magnetic resonance therapy.

FIG. 8 shows a perspective view of a further embodiment of an apparatus 1 for nuclear magnetic resonance therapy.

The apparatus 1 for nuclear magnetic resonance therapy comprises a bed 2 which is arranged horizontally in this embodiment and on which a patient to be treated (not shown) can lie down with his entire body.

Bed 2 is part of a module comprising the housing 3. Adjacent to the bed 2 and adjacent to the housing 3, side walls 5 and 6 are arranged. The side walls 5 and 6 accommodate the sweep coils, as will be shown in detail below.

Furthermore, the outer housing 7 can be seen in this view, which is part of the housing which receives the side wall 6.

A coil casing 8 for generating an alternating magnetic field is arranged above side walls 5, 6.

A further coil for generating an alternating magnetic field, which cannot be seen here, is located below bed 2.

Furthermore, the module comprising the bed includes a control unit 4 which is arranged at the front end of this module.

Figure 9:
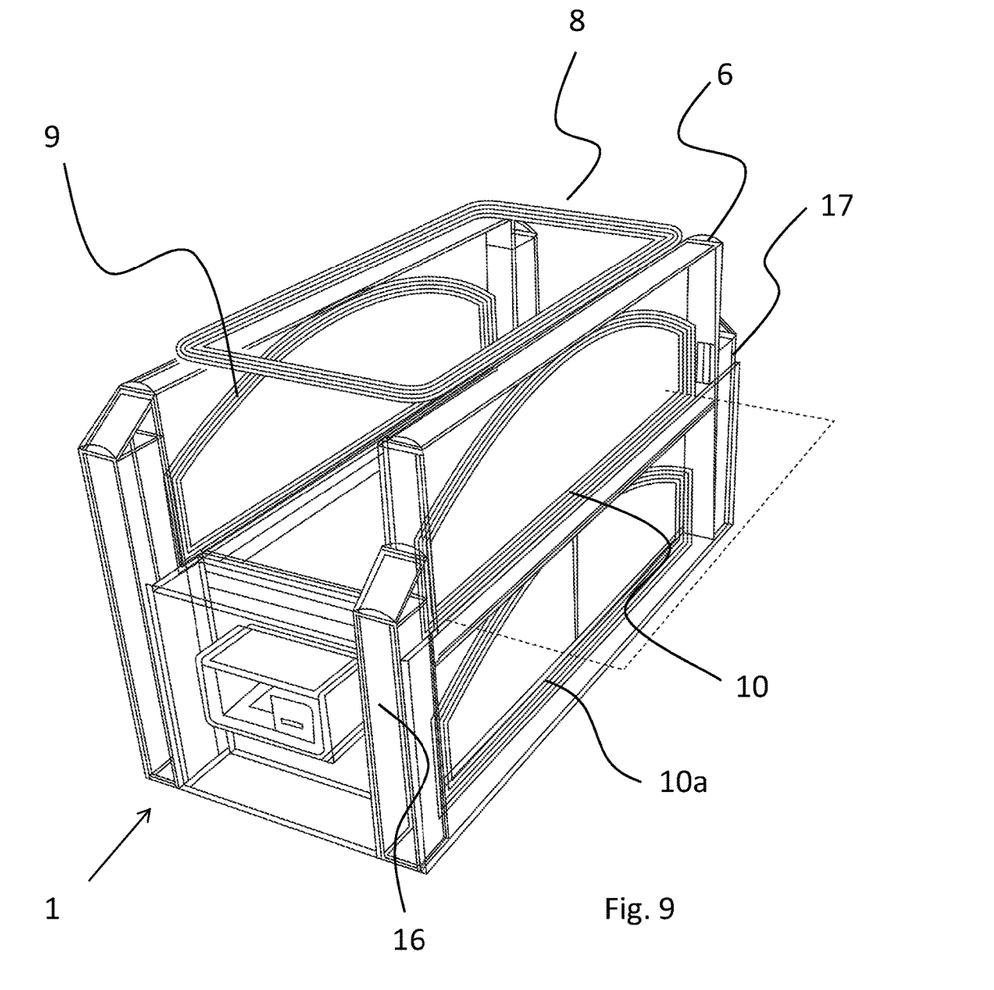
FIG. 9 shows a further perspective view of an apparatus for nuclear magnetic resonance therapy in a wireframe view in which even hidden edges can be seen.

FIG. 9 is a wireframe view of the apparatus 1 for nuclear magnetic resonance therapy shown in FIG. 8, where hidden edges, i.e. the interior of the apparatus 1 for nuclear magnetic resonance therapy, can now be seen in the manner of an X-ray image.

Now, the two sweep coils 9 and 10 arranged within side walls 5, 6 can be seen.

Furthermore, this view illustrates that the side wall 6 is located between two columns 16, 17 and can be moved downwards so that the sweep coil 10 will then be in the position 10*a*.

For moving down, i.e. lowering the side part, various technical options are conceivable. For example, manual lowering is conceivable. For this purpose, the side part may run in rails and may be coupled with a counterweight, via a cable and a pulley. The counterweight prevents the side part from coming down and allows to easily raise and lower it manually.

Furthermore, motorized actuation is conceivable as well, for example using a spindle drive.

The sweep coils 9 and 10 are arranged opposed to each other in a Helmholtz configuration and cover a large part of the length of the bed surface.

Coil casing 8 also extends over a large part of the length of the bed and almost across the entire width of the bed.

Figure 10:
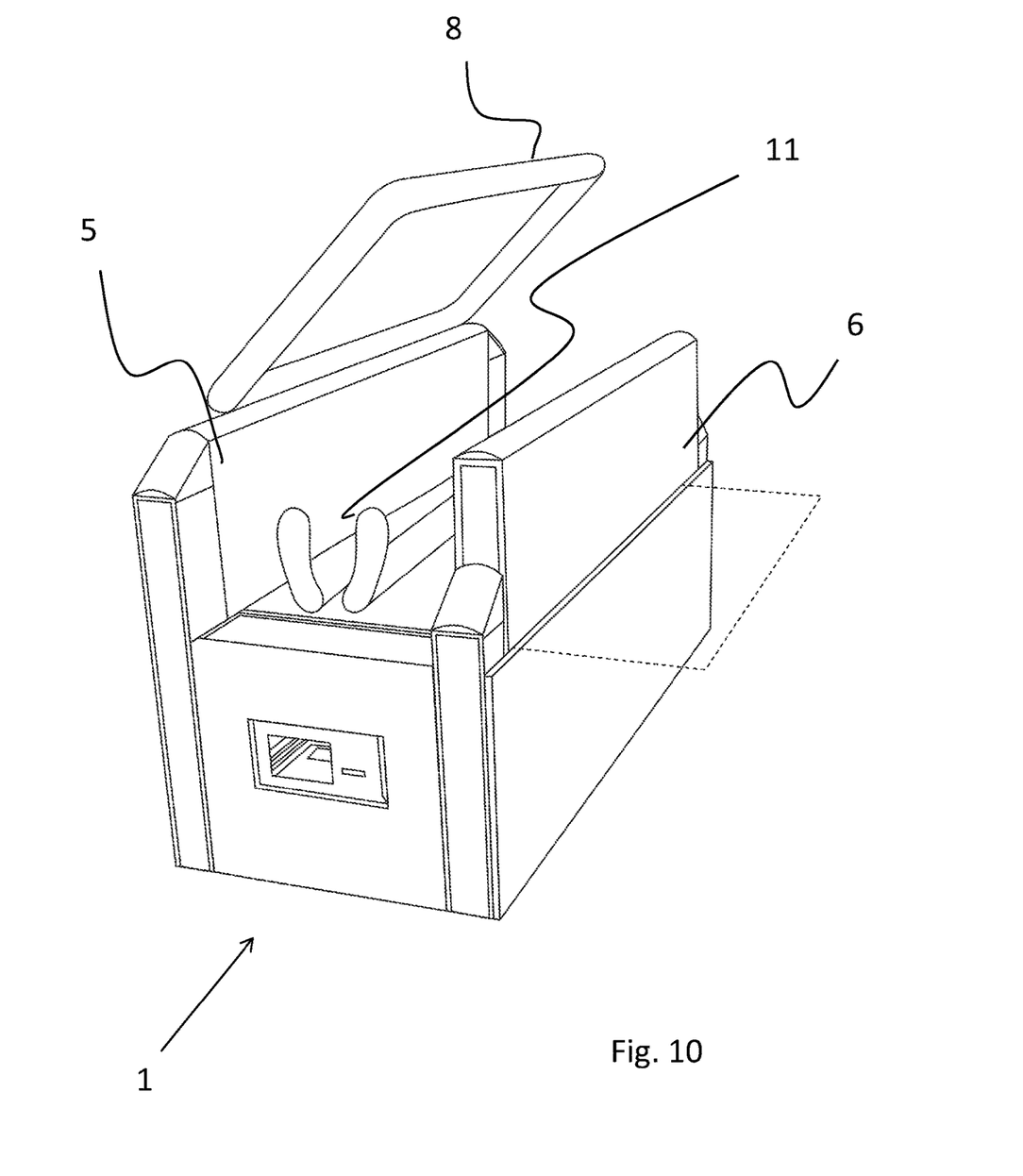
FIG. 10 shows the apparatus for nuclear magnetic resonance therapy of FIG. 9 with the upper coil for generating an alternating magnetic field pivoted upwards.

FIG. 10 shows the apparatus 1 for nuclear magnetic resonance therapy illustrated in FIGS. 8 and 9, now with the upper coil casing 8 including a coil for generating an alternating magnetic field pivoted upwards. For this purpose, the coil casing 8 is hinged on side wall 5.

When the side wall 6 is lowered now, the user 11 can easily get into the apparatus for nuclear magnetic resonance therapy.

Figure 11:
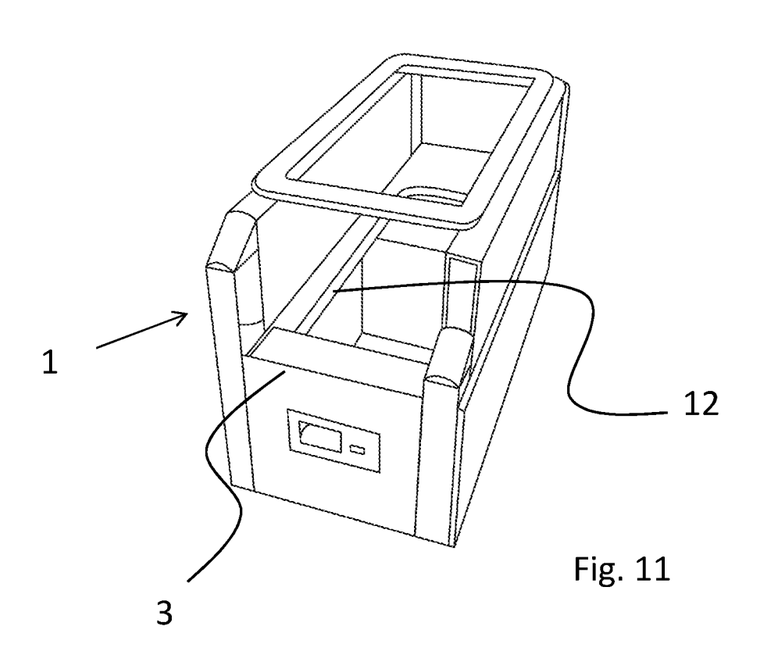
FIGS. 11 and 12 show two further perspective views of an apparatus for nuclear magnetic resonance therapy.

FIG. 11 shows a further perspective view of an apparatus for nuclear magnetic resonance therapy, in which the bed surface of the housing 3 which is configured as a module has been removed.

Now, it can be seen that a coil 12 for generating an alternating magnetic field is arranged below the bed surface as well. This coil is synchronized with the upper coil for generating an alternating magnetic field in a Helmholtz configuration.

Now, an alternating magnetic field with quite homogeneous field strength is achieved in the treatment volume, which vertically superimposes the field of the sweep coils arranged in the side parts.

Figure 12:
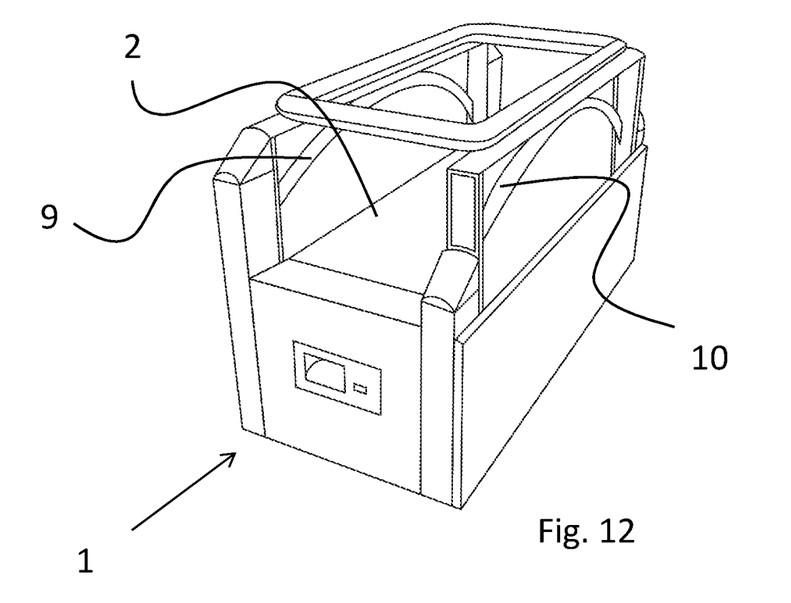

FIG. 12 is a view of an apparatus 1 for nuclear magnetic resonance therapy, in which now the sweep coils 9 and 10 can be seen, between which the treatment volume is defined on bed 2.

Figure 13:
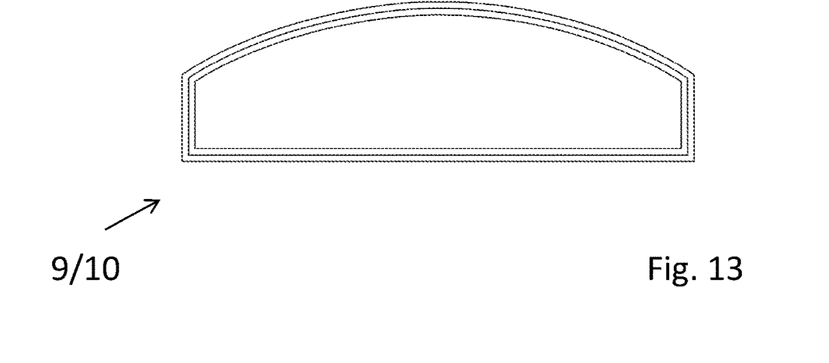
FIG. 13 is a view of a sweep coil.

FIG. 13 shows the configuration of the sweep coils.

They have the shape of a segmental arc window, that is to say they have a rectilinear lower portion and a curved upper portion, and between the arc and the lower portion the coils have a straight portion.

However, it is likewise conceivable to design the coil as a segmental arc and/or at least to round off the angular areas.

Figure 14:
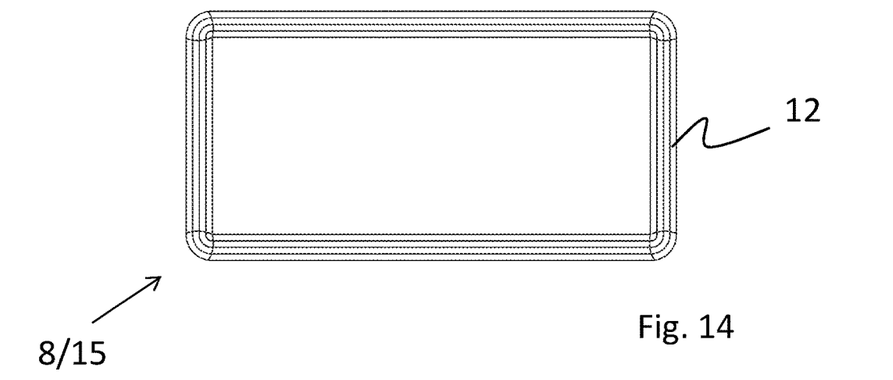
FIG. 14 shows the coil casing of a coil for generating the alternating magnetic field.

FIG. 14 shows the coil casing 8, 15 of the upper and/or lower coils for generating an alternating magnetic field.

The coil casing has a ring-type shape with a substantially rectangular geometry and is substantially adapted to the shape of the bed surface. The housing with central opening accommodates the coil 12 for generating the alternating magnetic field.

Figure 15:
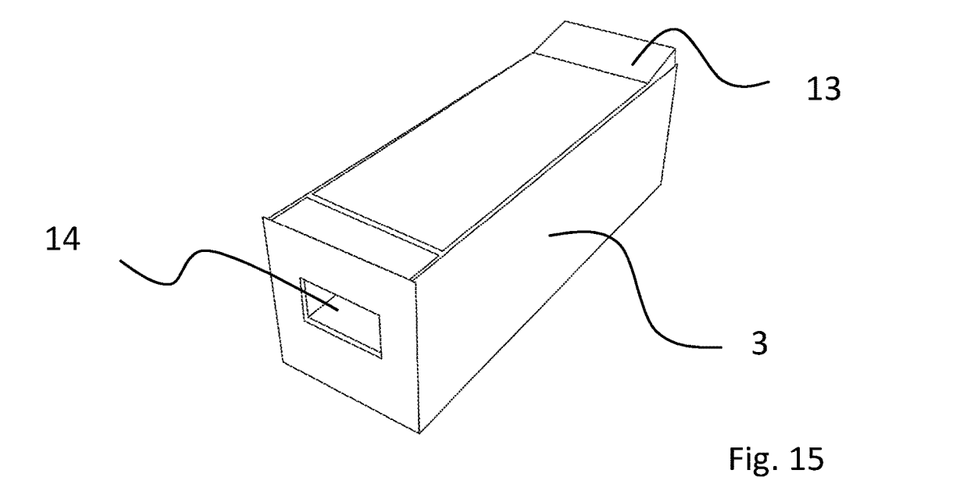
FIG. 15 is a perspective view of a module comprising the bed.

FIG. 15 shows the housing 3 of the bed surface module, which comprises a headrest 13 and, on the opposite end, a receiving slot 14 for the control unit (4 in FIG. 8).

This module may be turned around about 180° so that the control unit will be located at the desired side.

Figure 16:
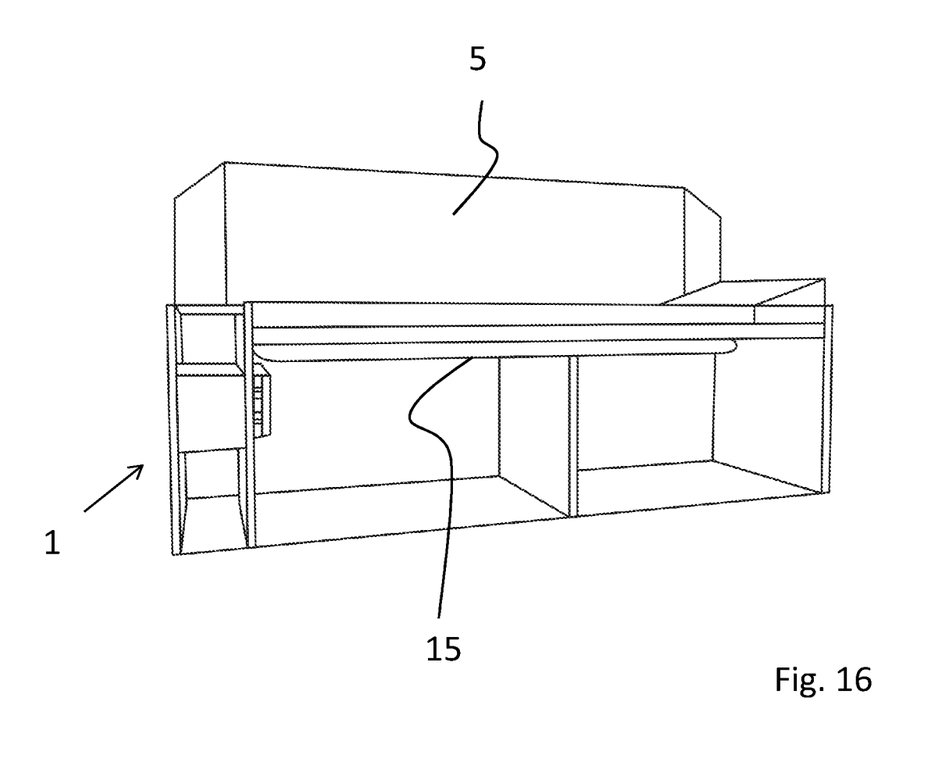
FIG. 16 is a sectional view of the apparatus for magnetic resonance therapy.

FIG. 16 shows a sectional view of an apparatus 1 for nuclear magnetic resonance therapy 1. Here, the coil casing 15 arranged below the bed surface can be seen, which accommodates the lower coil for generating an alternating magnetic field. Also, a side wall 5 can be seen, in which a sweep coil is located.

The treatment volume extends from the coil 15 to above the bed and is located between the side walls.

In addition, it should be noted that in an alternative embodiment variant which is not shown in the drawings, the side wall designated by reference numeral 6 is coupled to the upper coil casing (reference numeral 8) and can be pivoted upwards therewith.

The invention permitted to provide an apparatus for nuclear magnetic resonance therapy which allows to achieve large treatment areas, and which in particular enables a whole-body treatment and provides simplified access for the patient.

LIST OF REFERENCE NUMERALS

1 Apparatus for nuclear magnetic resonance therapy
2 Bed surface
3 Housing
4 Control unit
5 Sidewall
6 Sidewall
7 Outer housing
8 Coil casing
9 Sweep coil
10, 10*a*-*b* Sweep coil
11 User
12 Coil
13 Headrest
14 Receiving slot
15 Coil casing
16 Column
17 Column
20 Bed
21 Pedestal 22 Angular part
23a, 23b Coil casing
24 Coil casing
25 Pivot joint
26 Screen
27 Rear part
28a, 28b Arm
29a-29d Traction gas spring
30 Beam
31 Pivot joint
32 Frame
33 Bulge
34 Rod
35 Housing part
36 Opening
37 Handle
38 Light strips

The invention claimed is:

1. An apparatus for nuclear magnetic resonance therapy, comprising
a bed,
lateral coils that are arranged laterally of the bed, with a space between the lateral coils defining a treatment volume,
a first further coil arranged below the bed, and
a second further coil arranged above the treatment volume,
wherein the second further coil is pivotally mounted to the bed and configured to pivot between a lowered position, in which the second further coil is arranged substantially parallel to the first further coil, and a raised position, in which the second further coil is upwardly pivoted away from the lowered position, and
wherein the second further coil and one of the lateral coils are mounted in perpendicular planes to an angular part and jointly pivot between the lowered position and the raised position.

2. The apparatus for nuclear magnetic resonance therapy as claimed in claim 1, wherein at least the second further coil is arranged in a ring type casing having an inner opening and a substantially rectangular shape when seen in a plan view.

3. The apparatus for nuclear magnetic resonance therapy as claimed in claim 1, wherein the angular part is coupled to the bed via a pivot joint having a pivot axis.

4. The apparatus for nuclear magnetic resonance therapy as claimed in claim 3, wherein the angular part is adapted for being pivoted upwards from the lowered position to the raised position by an angle of at least 50°.

5. The apparatus for nuclear magnetic resonance therapy as claimed in claim 1, wherein the angular part comprises at least one operating unit.

6. The apparatus for nuclear magnetic resonance therapy as claimed in claim 1, wherein the angular part is adapted for being held in an upwardly pivoted position by at least one traction gas spring.

7. The apparatus for nuclear magnetic resonance therapy as claimed in claim 1, wherein at least one coil selected from the lateral coils, the first further coil, and the second further coil is embedded in a potting compound.

8. The apparatus for nuclear magnetic resonance therapy as claimed in claim 1, wherein the apparatus comprises a sensor for detecting whether the second further coil is in the raised position or the lowered position.

9. The apparatus for nuclear magnetic resonance therapy as claimed in claim 1, wherein the apparatus comprises a control unit which is used to measure an amperage of one of the coils or a frequency of an alternating field generated by at least one of the coils, at least upon start-up of the apparatus.

10. The apparatus for nuclear magnetic resonance therapy as claimed in claim 1, wherein the treatment volume has a length between 1.4 and 2.5 m, a width between 0.4 and 1 m, and a height between 0.4 and 1 m.

11. The apparatus for nuclear magnetic resonance therapy as claimed in claim 3, wherein the pivot axis is arranged in a plane above the lateral coils.

12. The apparatus for nuclear magnetic resonance therapy as claimed in claim 3, wherein the bed is laterally accessible when the angular part is in the raised position and is laterally inaccessible when the angular part is in the lowered position.

13. The apparatus for nuclear magnetic resonance therapy as claimed in claim 1, wherein the second further coil is pivotally mounted to the bed by a frame.

* * * * *